(12) United States Patent
Ingenhoven et al.

(10) Patent No.: US 7,374,724 B2
(45) Date of Patent: May 20, 2008

(54) DEVICE FOR PROCESSING SAMPLES, USE OF THE DEVICE, AND METHOD FOR PRODUCING THE DEVICE

(75) Inventors: Nikolaus Ingenhoven, Männedorf (CH); Dieter Lubda, Bensheim (DE)

(73) Assignees: Tecan Trading AG, Mannedorf (CH); Merck Patent GmbH, Darmstadt (DE)

( * ) Notice: Subject to any disclaimer, the term of this patent is extended or adjusted under 35 U.S.C. 154(b) by 364 days.

(21) Appl. No.: 10/156,588

(22) Filed: May 28, 2002

(65) Prior Publication Data

US 2002/0182114 A1 Dec. 5, 2002

Related U.S. Application Data

(60) Provisional application No. 60/304,979, filed on Jul. 12, 2001.

(30) Foreign Application Priority Data

May 29, 2001 (CH) ..................... 0990/01

(51) Int. Cl.
*B01L 11/00* (2006.01)
(52) U.S. Cl. .................. 422/101; 422/99; 422/100; 210/198.2; 210/656; 436/174
(58) Field of Classification Search .......... 422/99–101; 210/198.2, 656; 436/174
See application file for complete search history.

(56) References Cited

U.S. PATENT DOCUMENTS 4,091,677 A 5/1978 Oshikubo (Continued)

FOREIGN PATENT DOCUMENTS

DE 3717211 A1 12/1988

(Continued)

OTHER PUBLICATIONS

"ZipTips Pipette Tips" Millipore Catalogue, 'Online! XP002192545.

(Continued)

*Primary Examiner*—Jill Warden
*Assistant Examiner*—Jyoti Nagpaul
(74) *Attorney, Agent, or Firm*—Notaro & Michalos P.C.

(57) ABSTRACT

The invention relates to a device (1) for processing samples (2), comprising a body (3) with a collecting chamber (4), which can be connected with a pump (5) for aspirating, or dispensing fluids and that acts on this collecting chamber, a separating chamber (6) adjoining the collecting chamber (4) for the solid phase extraction and elution of organic, or inorganic particles (7) separated from these samples (2), and an opening (8) for releasing these particles (7). The device in accordance with the invention relates to individual pipette tips, as well as to SPE microplates, and is distinguished in that the device (1) comprises a capillary (9), which is connected with the collecting chamber (4), or with the body (8), and has a packing (10) for the solid phase extraction of organic, or inorganic particles (7) separated from these samples (2) and is used as a separating chamber (6). In accordance with the invention, the package (10) can be adapted to the chemical-physical nature of the organic, or inorganic particles (7) to be extracted, as well as to a defined minimum volume.

18 Claims, 3 Drawing Sheets

U.S. PATENT DOCUMENTS

| | | | |
|---|---|---|---|
| 5,260,028 A * | 11/1993 | Astle ..................... | 422/81 |
| 5,603,899 A | 2/1997 | Franciskovich et al. | |
| 5,918,273 A | 6/1999 | Horn | |
| 6,416,716 B1 * | 7/2002 | Shukla et al. ............ | 422/101 |
| 6,531,060 B1 | 3/2003 | Nakanishi et al. | |
| 6,562,744 B1 | 5/2003 | Nakanishi et al. | |
| 2001/0001643 A1 | 5/2001 | Simpson et al. | |
| 2003/0190757 A1 | 10/2003 | Furuno et al. | |

FOREIGN PATENT DOCUMENTS

| | | |
|---|---|---|
| EP | 1 033169 A1 | 9/2000 |
| EP | 1329714 A1 | 7/2003 |
| EP | 1382963 A1 | 1/2004 |
| WO | WO 94/20831 A1 | 9/1994 |
| WO | WO 97/26540 A1 | 7/1997 |
| WO | WO 98/37949 A1 | 9/1998 |
| WO | WO-99/38006 A1 | 7/1999 |
| WO | WO-99/50654 A1 | 10/1999 |

OTHER PUBLICATIONS

Search Report of EP 1 033 169 A.
Search Report of EP 02 01 1729.

* cited by examiner

DEVICE FOR PROCESSING SAMPLES, USE OF THE DEVICE, AND METHOD FOR PRODUCING THE DEVICE

REFERENCE TO RELATED APPLICATIONS

This patent application claims priority from Swiss patent application No.: CH 0990/01 filed May 29, 2001 and from U.S. Provisional Application Ser. No.: 60/304,979 filed Jul. 12, 2001.

FIELD OF THE INVENTION

The invention relates to a device for processing samples, in particular for solid phase extraction, elution and application of target molecules. The invention also relates to the use of the device for processing samples, and to a method for producing this device.

BACKGROUND OF THE INVENTION

In laboratories which are occupied with molecular- biological/biochemical research, the fields of "genomics" or "proteomics" are commonly used terms for processing and research into idioplasm, such as DNA (deoxyribonucleic acid), RNA (ribonucleic acid), or their parts in the form of oligonucleotides or of proteins (albumins, for example in the form of antigens or antibodies, or their parts in the form of polypeptides). Such and similar processes can comprise a multitude of work steps at various work stations. The field of proteomics in particular is gaining in importance, because not only the genome (idioplasm), but primarily the respectively provided protein setup (proteome), determine the appearance and the state of a biological organism. This knowledge led to the necessity that today a deeper understanding of proteins as the actual regulation networks taking the place of the dogma "one gene—one protein—one function".

Proteomics—the quantitative analysis of the proteins present in an organism at a defined time and under defined conditions—will therefore distinguish itself as an important key for functional analysis in basic research (for example in connection with the elucidation of reaction and regulation networks), as well as in applied research (for example in connection with the search for and selection of targets for the development of medicaments).

Systems which are capable of performing automated separation, or separation and cleaning methods, typically employ so-called "SPE plates" (Solid Phase Extraction plates) for processing samples, in particular for solid phase extraction. The principle of solid phase extraction can be summarized as follows: A sample is applied to a solid sorbent, which adsorbs or binds defined components of the sample. These components are often called target molecules, however such components might be non-ionic as well as ionic species or particulate matter like cells, cellular substructures like mitochondria or nuclei, or virus particles. In the following disclosure the term "particles" is understood to cover all types of target molecules mentioned above. In performing solid phase extraction after this binding step the remainder of the sample is separated from the solid sorbent. The next step most commonly applied is washing of the solid phase loaded with the particles. Finally the particles are eluted from the solid sorbent. The resulting fluid contains a purified and/or concentrated fraction containing the particles, e.g. the target molecules. In the process—depending on the target of the application—a sorbent, e.g. a specifically activated filter or an appropriate screen is placed in, or at least close to, the bottom outlet opening of a small cup or "well" of a microplate (see FIG. 1). To perform a separating process, a sample is pipetted into a well and is forced to leave the well of the microplate through the sorbent via the bottom outlet opening. Typically suction forces (by the application of a vacuum) or positive pressure or gravity (e.g. by means of centrifuging) are used for this purpose.

In the course of this process, the target molecules therefore adsorb or bond to the activated material. After performing some washing steps, the target molecules, or the organic, or inorganic particles separated from the sample as described above, can be eluted with the aid of an eluent (a suitable solvent), i.e. separated from the filter, or the screen. The eluted particles are subsequently transferred onto a second microplate or to the surface of a support as described above.

Usually the sorbents used as packings in solid phase extraction comprise a base material, which should be inert to the sample components, and binding groups on the base material. These binding groups bind specifically the particles, e.g. target molecules. Sometimes the base material itself binds the target molecules, e.g. nucleic acids are reversably bound by silica ($SiO_2$). Porous or non-porous particulate materials or other porous formed bodies made of organic or inorganic compounds usually form the base material. Examples of organic polymers are styrene-divinylbenzene copolymers or hydrophilic copolymers based on poly-(meth)acrylates, or polyamides. Porous membranes, fibrous materials, e.g. woven or non-woven fabrics or felts can also be used as organic base materials. Typical examples of inorganic base materials are metal oxides, especially $SiO_2$ or $Al_2O_3$. The binding groups can be directly introduced to the base material, e.g. by sulfonating aromatic groups of styrene-divinylbenzene copolymers. Binding groups can also be introduced to the base material by polymerizing suitable monomers onto the base material. Inorganic base materials can be modified using organic substituted silanes containing e.g. ionic groups. Sorbents usable in solid phase extraction are basically available commercially or are described in the literature.

Often the filters, or screens, employed with known SPE plates have different flow resistances so that—in case a vacuum was used for emptying the SPE plates—some wells are emptied more rapidly than others. Then the emptying of all wells can only be achieved by the sudden application of a strong vacuum. But this often leads to a spraying, or even foaming, eluate, which can lead to undesired material transfer to neighboring wells, or to a loss of the sample.

WO 98/37 949 discloses a pipette tip which contains a sorbent. Said sorbent consists of a composite casted in place, whereby said composite consists of a plurality of sorptive particles entrapped in a porous polymer matrix.

Also known are so-called "ZipTips™", which are sold by the Millipore firm (Millipore Corporation, 80 Ashby Road, Bedford, Mass. 01730-2271, USA)(see FIG. 2). Such "throwaway tips" are placed on a pipette and have a large interior of approximately 10 to 20 µl. If the tips are not completely filled with fluid, an air cushion remains between the fluid surface and the piston of the pipette. This air cushion acts like a damping element during aspirating (picking up) and dispensing (releasing) of the fluid. For this reason the determination of the end point of picking up and releasing fluids—in particular if only small volumes are intended to be pipetted—requires great skill and effort, if it can be reproduced at all.

Features necessary for improving sorbents in solid phase extraction are:
- low unspecific binding of sample components to the base material;
- high binding capacity including dynamic binding capacity at high linear flow rates (the latter describes the loss of binding capacity at elevated linear flow rates);
- low hydrodynamic resistance to allow high linear flow rates at low pressure drop;
- especially in microplate assemblies the hydrodynamic resistance of the sorbent in each well should vary little between different wells.

OBJECT AND SUMMARY OF THE INVENTION

It is the object of the invention to propose an alternative device which permits the alleviation, at least in part, of the disadvantages of the devices described as the prior art.

This object is attained by proposing a device for processing samples, which comprises a body with a collecting chamber, which optionally can be connected with a pump for aspirating, or dispensing fluids and acts on this collecting chamber, a separating chamber adjoining this collecting chamber for the solid phase extraction and elution of organic, or inorganic particles separated from these samples, and an opening for releasing these particles. The device in accordance with the invention is distinguished in that it comprises a capillary, which is connected with the collecting chamber, or with the body, and has a packing for the solid phase extraction of organic, or inorganic particles separated from these samples, and is used as the separating chamber. Additional characteristics in accordance with the invention ensue from the dependent claims.

The capillaries used in this invention contain the sorbent selected in order to allow reversible binding of the particles (e.g. target molecules). Examples of target molecules and useful binding groups are:

Nucleic acids (RNA, DNA): Silica as sorbent, or sorbents containing binding groups like cationic groups (anion exchange materials) or affinity ligands (oligonucleotides or analogues thereof like (hetero)aromatic polyamides).

Proteins: ionic groups (anion or cation exchange materials), hydrophobic interaction or reversed phase materials, affinity ligands like antibodies or antibody fragments, metal chelates, dyes or substrate analogues.

Low molecular weight compounds like pharmaceuticals or their metabolites: Restricted access materials.

Sorbents as listed above are basically known in the art. Details concerning ion exchange sorbents for example are disclosed in EP 0 337 144 (corresponding U.S. Pat. No. 5,453,186), EP 0 686 258, EP 0 722 360 (corresponding U.S. Pat. No. 5,647,987), and EP 0 804 494 (corresponding U.S. Pat. No. 5,866,673). Sorbents containing affinity ligands and typical affinity ligands are disclosed in EP 0 565 978 (corresponding U.S. Pat. No. 6,291,216), hydrophobic interaction sorbents are disclosed in EP 0 708 919 (corresponding U.S. Pat. No. 5,641,403), and for restricted access modes in EP 0 537 461 (corresponding U.S. Pat. No. 6,074,555).

As far as particulate sorbents are concerned the capillaries have to be closed by means which allow fluids to pass through and which retain the sorbent in the capillary; examples of such means are: constrictions at at least one end of the capillary or porous plugs. The latter are disclosed in WO 01/57 516. Particulate sorbents can also be sintered or glued together in order to fix them in the capillary.

Monolithic sorbents can be produced in the capillaries in situ. They have to have macropores to allow the flow of fluids through the capillary. Their surface might be enlarged by mesopores on the surface of the solid structure. Monolithic sorbents based on silica are disclosed in WO 99/38 006 and WO 99/50 654.

The dimensions of the capillaries used in the device according to the invention are primarily determined by the volume of the sample to be handled and to the dimensions of the wells. Typically the length of the capillaries would be between 0.5 mm and 5 cm, their inner diameter between 1 and 500 µm, and their outer diameter corresponding to inner diameter and thickness of the walls of the capillary used.

Counted among the advantages of the device in accordance with the invention over the prior art are:

The volume of the bed (packing) and the bottom outlet opening (diameter) of the device can be individually matched to the chemical-physical nature of the organic, or inorganic particles to be extracted. By means of this it is possible to prevent the loss of the target molecules (by adsorption in too large bed volumes) and the appearance of dead volumes (such as occurs between the packing and the bottom outlet opening as a condition of the production of the device in accordance with the prior art).

It is possible to manufacture large numbers of structurally identical microplates, in which only the inserted capillaries vary as a function of the chemical/physical nature and/or the volume of the organic, or inorganic particles to be extracted.

Cleaning of the samples (peptide desalinization and concentration) for "MALDI TOF-MS", "Matrix Assisted Laser Desorption Ionization—Time of Flight Mass Spectrometry" is customarily performed with "Zip-Tips™" from Millipore. This known solution is disadvantageous because of the high single price, bed volume and flow resistance, but also because of the limiting single channel operation, and it can be replaced by the proposed device in accordance with the invention.

The required capillaries to be filled with the respective packing have been available in commerce for many years (for example from Polymicro Technologies, 18019 N. 25th Avenue, Phoenix, Ariz. 85023-1200, USA).

Thanks to the proposed method for producing the device in accordance with the invention it is now possible to employ these capillaries together with individual pipette tips or with microplates. Such microplates are also known as microtiter plates™ (trademark of Beckman Coulter Inc., 4300 N. Harbour Boulevard, P.O. Box 3100, Fullerton, Calif. 92834, USA) and can comprise 96, 384 or 1536 wells, for example.

A reproducible minimal eluting volume of approximately 0.5 µl allows—preferably with the simultaneous arrangement of many parallel channels—the greatest amount of automation of the process and a minimization of the process times.

The release (dispensation) of smallest amounts of the eluate permits the successful prevention of a thinning effect, and therefore the omission of critical concentration methods, in which the target molecules (for example proteins) often coagulate, or adsorb to the container walls, and are therefore lost.

The release by means of the capillaries can be performed, for example, directly onto the surface of a MALDI TOF-MS target, so that intermediate pipetting steps for the smallest samples (as with the SPE plates of the prior art) are no longer necessary.

A further object of the invention is to propose the novel use of the device in accordance with the invention for processing samples. This object is attained by means of the characteristics of claim 14.

A still further object of the invention is to propose a method for producing the device in accordance with the invention for processing samples. This object is attained by means of the characteristics of claims 16 and 17.

Advantageous embodiments of the invention are the subject of the dependent claims.

Without further elaboration, it is believed that one skilled in the art can, using the preceding description, utilize the present invention to its fullest extent. The preferred specific embodiments and examples are, therefore, to be construed as merely illustrative, and not limitative of the disclosure in any way whatsoever.

The entire disclosures of all applications, patents, and publications cited above and below, and of corresponding applications Swiss CH 2001 0990/01 filed May 29, 2001, and U.S. Ser. No. 60/304,979, filed Jul. 12, 2001, are hereby incorporated by reference.

The following schematic drawings are intended to document the known prior art. Preferred embodiments of the device in accordance with the invention will also be explained by means of the drawings, without this being intended to limit the scope of the invention.

DETAILED DESCRIPTION OF THE PREFERRED EMBODIMENTS

Figure 1:
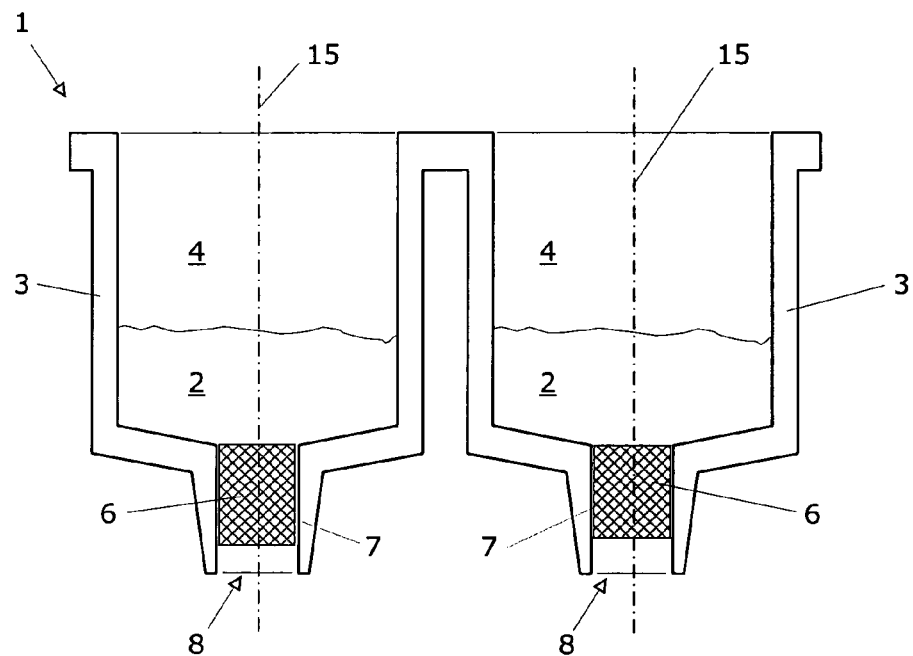
FIG. 1 is a partial vertical section through an SPE plate of the prior art.

FIG. 1 is a partial vertical section through an SPE plate of the prior art. This SPE plate therefore is a device 1 for processing samples 2, which comprises a body 3 with a collecting chamber 4. Moreover, the device 1 comprises a separating chamber 6, adjoining the collecting chamber 4, for solid phase extraction and elution of organic, or inorganic particles 7 separated from these samples 2, and an opening 8 for releasing these particles 7. As described at the outset, a specifically activated filter, for example, which defines the separating chamber 6, is placed close to the bottom outlet opening 8 of a small cup 4 or "well" 4 of a microplate. To perform a separating process, a sample is pipetted into a well 4 and is forced by means as described above, e.g. by the application of suction forces (by the application of a vacuum) or gravity (by means of centrifuging) to leave the microplate through the filter 6 via the bottom outlet opening 8.

Thus, the target molecules adsorb or bond to the activated material in the course of this process. After performing some washing steps, the target molecules, or the organic, or inorganic particles separated from the sample in this way, can be eluted with the aid of an eluent (a suitable solvent), i.e. separated from the filter, or the screen. The eluted particles are subsequently transferred onto a second microplate or to the surface of a support by means of vacuum or centrifuging.

The different flow resistances of the filters 6 used are illustrated by the different height of the filter underside and the opening 8. Actually this height (together with the interior diameter of the opening 8) defines an undesirable dead volume, in which a remnant of the eluate can be caught and therefore distort the result.

Figure 2:
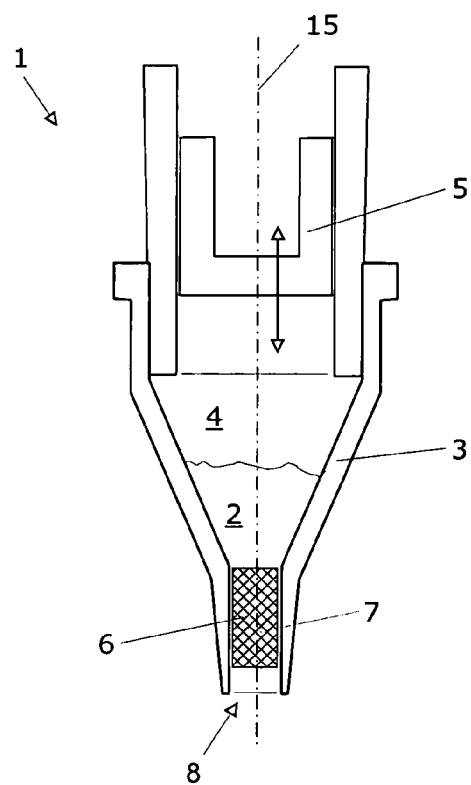
FIG. 2 is a vertical section through a "ZipTip™" of the prior art.

FIG. 2 shows a vertical section through a "ZipTip™" of the prior art. Thus, this ZipTip™ is a device 1 for processing samples 2, which comprises a body 3 with a collecting chamber 4. This collecting chamber 4 can be connected with a pump 5 acting on this collecting chamber (movement indicated by the two-headed arrow), for aspirating, or dispensing fluids. This connection with the pump is achieved by placing the ZipTip™ on a pipette, wherein the piston of the pipette constitutes the pump 5. Moreover, the device 1 comprises a separating chamber 6, adjoining the collecting chamber 4, for solid phase extraction and elution of organic, or inorganic particles 7 separated from these samples 2, and an opening 8 for releasing these particles 7.

As described at the outset, an air cushion in the ZipTip™ acts like a damping element during the aspiration (picking up) and dispensing (releasing) of fluid. Additional problems can occur in that the sealing surfaces between the ZipTip™ and the pipette do not perfectly seal, so that any reproducibility of the volumes to be pipetted becomes questionable. Furthermore, every ZipTip™ placed on it can be oriented in a direction deviating from the actual pipette axis 15, so that a true axial equipping of a multiple pipette can be quite complicated and time-consuming. The employed filter 6 is illustrated by the difference in height between the filter underside and the opening 8. Such ZipTips™ can also have different flow resistances and undesired dead volumes.

FIG. 3 shows a partial vertical section through a device of the invention in accordance with a first embodiment in the form of a single pipette tip. Here, this is a device 1 for processing samples 2, which comprises a body 3 with a collecting chamber 4, which can be connected with a pump 5 for aspirating, or dispensing fluids. Moreover, the device 1 comprises a separating chamber 6, adjoining the collecting chamber 4, for solid phase extraction and elution of organic, or inorganic particles 7 separated from these samples 2, and an opening 8 for releasing these particles 7. This device is distinguished in that it comprises a capillary 9 connected with the collecting chamber 4, or the body 3, which has a packing 10 for the solid phase extraction of organic, or inorganic particles 7 separated from these samples 2 and is used as the separating chamber 6.

Figure 3A:
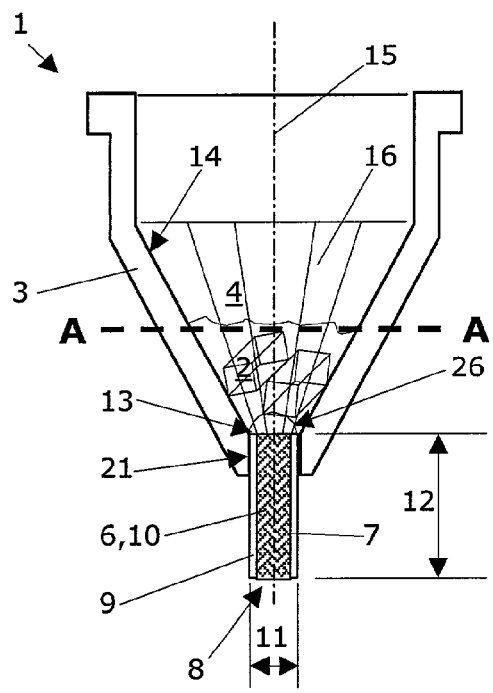
FIG. 3A is a partial vertical section through a device in accordance with the invention in accordance with a first embodiment.
Figure 3B:
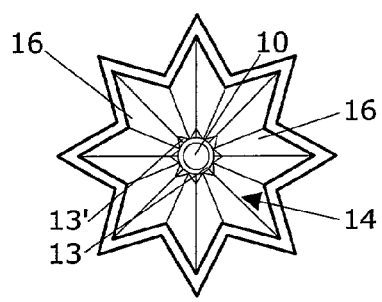
FIG. 3B is a horizontal section through the collecting chamber of the device of the invention in accordance with a first embodiment corresponding to the section line A-A in FIG. 3A.

As is well visible in FIG. 3A, with this device 1 the packing 10 of the capillary 9 immediately adjoins the collecting chamber 4 and completely fills the capillary 9. This packing 10 can be easily matched to the chemical-physical nature of the organic, or inorganic particles 7 to be extracted simply by using a capillary with the suitable properties. With the capillaries provided by the firm Polymicro Technologies, the exterior diameters (for example 150

μm, 363 μm) are identical over a wide range of the interior diameters (2 to 75 μm, 5 to 150 μm), so that the geometry of the device need no change, although quite different bed volumes, or packing types, can be used. Thus, a capillary 9 can always have the same outer diameter 11; then the packing volume can be determined by means of the length 12 and/or the interior diameter of the capillary 9. A capillary 9 is preferably connected with the collecting chamber 4 by being inserted into the body 3, or by extrusion-coating the body 3 around it, wherein insertion is particularly preferred (see FIG. 6). For example, for incubating gel cubes (for example from a 2-D gel electrophoresis), bio-beads or filter paper scraps (for example from chromatography tests), and similar separating devices comminuted in this way, with organic, or inorganic particles 7 fractionated therein, at least a portion of the interior surface 14 of the body 3, or of the collecting chamber 4, preferably comprises a relief structure 16 essentially extending coaxially in respect to the longitudinal axis 15 of the body 3. This relief structure can have a serrated (see FIG. 3B) or corrugated (not represented) structure, or can also differ from these shapes; the important thing is that the interior surface 14 of the body, or of the collecting chamber 4, has elevations and depressions which prevent the gel cubes or other sample portions from blocking the removal of the eluate at the termination of the incubation.

At least one ring-shaped area 13 of the capillaries 9 and/or an area 13' of the interior surface 14 of the body 3 directly adjoining these capillaries can be made hydrophobic. This has the advantage that aqueous fluids have a curved surface 25 because of their surface tension and in this way can be layered on the capillaries, without the capillaries being filled. This is of particular advantage if the samples comprise filter paper scraps, gel cubes and like materials with organic, or inorganic particles 7 contained, or fractionated therein, and an incubation of these samples is intended to be performed in a volume as small as possible. For this, but also for other applications, it is advantageous if the body 3, or the collecting chamber 4 has (as represented) a V-shape, which adjoins the capillaries 9 in the area of its narrowest part.

Figure 4:
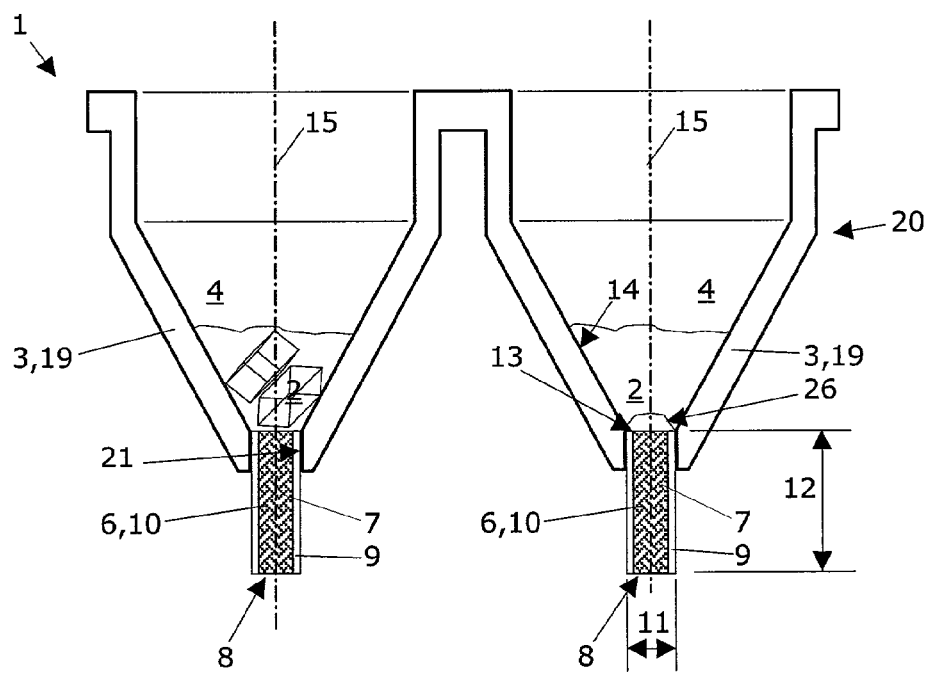
FIG. 4 is a partial vertical section through a device of the invention in accordance with a second embodiment.

FIG. 4 shows a partial vertical section through a device of the invention in accordance with a second embodiment, wherein the body 3 is designed as a well 19 of a microplate 20. Thus, the second embodiment is essentially a multiplication of the first embodiment, wherein a multiplication by the factors 96, 384 or 1536—corresponding to the number of wells in the microplate—is especially preferred. A ring-shaped area 13 of the capillaries 9 and/or an area 13' of the interior surface 14 of the body 3 directly adjoining these capillaries can be made hydrophobic in order to create an air bubble 25, which does not present an obstacle during the subsequent aspiration of the eluate.

Figure 5:
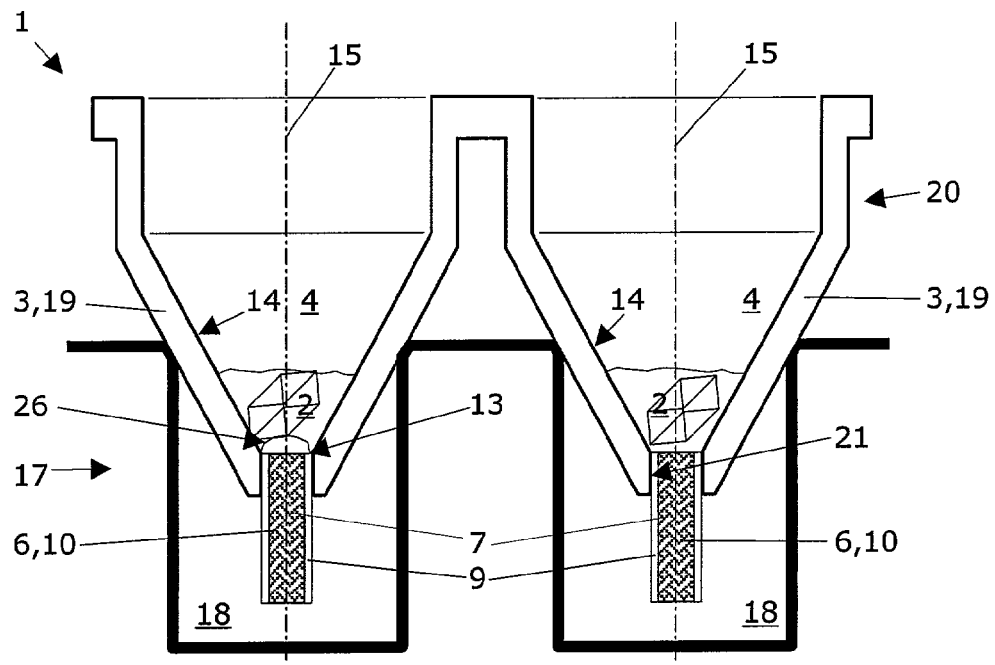
FIG. 5 is a partial vertical section through a device of the invention in accordance with a third embodiment.

As represented in FIG. 5, the device—in accordance with a third embodiment—can moreover comprise a support element 17 with at least one depression 18, into which the device 1 can be sealingly inserted without the capillaries 9 being touched. It has been shown that the filled wells 19 do not become empty in the course of an incubation process, if this sealing connection between the support element 17 and the wells 19 is made. The prevention of the capillaries 19 being touched protects them against mechanical damage.

A single depression 18 is of course sufficient for a single tip. If the device 1 consists of the combination of a microplate 20 with capillaries 9, the support element 17 is preferably embodied as a support plate which has respectively one depression 18 per well 19 of the microplate 20. Such support elements, or support plates, are preferably made of polypropylene, or polypropylene foam (with closed pores) and similar solid, or elastic plastic materials. They can also be used as support for mounting the capillaries 9 of a first method in accordance with the invention (see FIG. 6).

Figure 6:
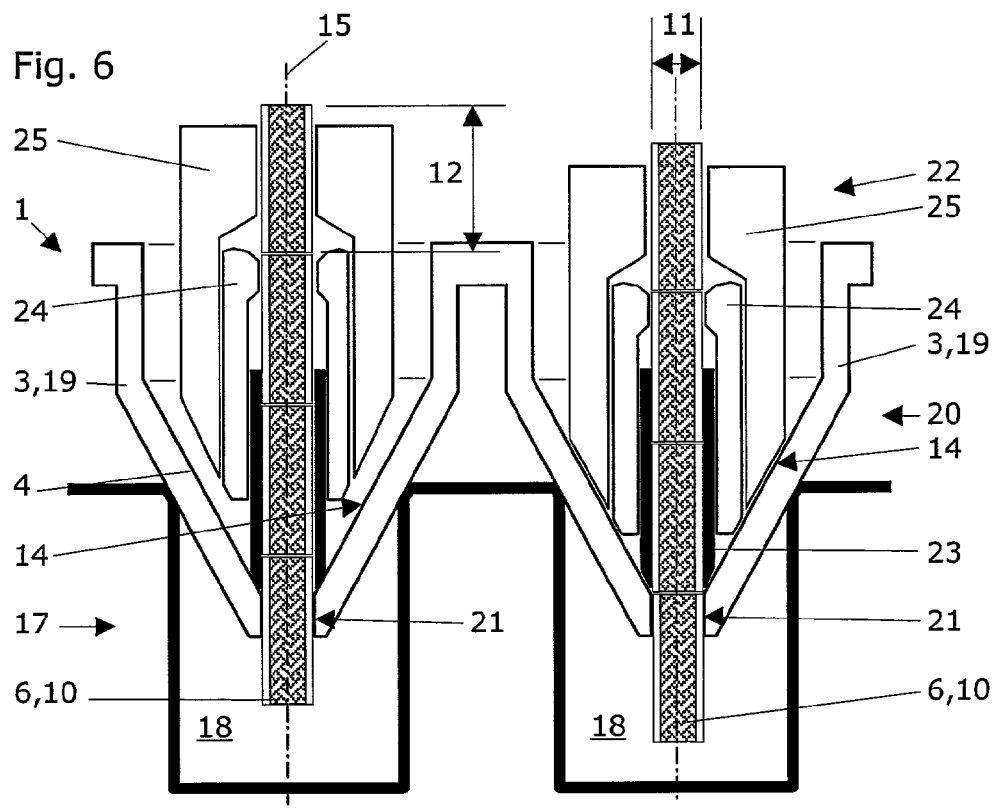
FIG. 6 is a partial vertical section through an arrangement for producing the device of the invention in accordance with a third embodiment.

FIG. 6 represents a partial vertical section through an arrangement for producing the device 1 of the invention in accordance with one of the embodiments represented. The method is distinguished by the following production steps:

Dividing an endless capillary filled with a packing 10 of a defined diameter 11 into capillaries 9 of the desired length 12 of a few millimeters to a few centimeters;

Injection-molding a body 3 (for example a microplate 20) with a collecting chamber 4 and a receiving opening 21 for a partial capillary element 9;

Inserting the capillaries 9 through the collecting chamber 4.

Two phases of the insertion by means of a retractable pencil-like device are represented in FIG. 6: an insertion device 22 is lowered on the left until it has reached an end position (represented on the right side) and the lowermost capillary 9 is completely inserted and positioned. This insertion device 22 comprises a guide tube 23, a gripping device 24 and a stock reservoir 25. The guide tube 23 guides and centers the capillaries 9, which are supplied from the stock reservoir 25 and are held by means of the gripping device 24. The exteriors of the guide tube 23 and/or of the gripping device 24 and/or of the stock reservoir 25 are preferable dimensioned, or inclined, in such a way, that they can be inserted into the collecting chamber 4, or can act on its interior surface 14. It is particularly preferred that in the course of at least one of the elements guide tube 23, gripping device 24 and/or stock reservoir 25 acting on the interior surface 14 of the collecting chamber 4, the lowermost capillary 9 has just reached its final seat. So that the capillary 9 is held in this seat in a satisfactory manner, the receiving opening is preferably produced barely narrower than its final dimension and is widened to the final size by inserting the capillary 9.

A support element as already described in connection with FIG. 5, for example, is suited as a base and support for the microplate 20 to be processed as just described. Here, the depressions 18, which are arranged aligned with the wells 19 of the microplate 20, represent a secure support and protect the inserted capillaries 9 against mechanical damage. To protect the inserted capillaries it is possible, for example, to store, package and dispatch a microplate 20 equipped with capillaries 9 together with a support element 17.

An alternative method (not represented) for producing the device of the invention in accordance with one of the represented embodiments is distinguished by the following process steps:

Securing an endless capillary of a defined diameter 11 and filled with a packing 10 in an injection mold cavity;

Injection-molding a body 3 with a collecting chamber 4 around the secured endless capillary;

Cutting off a first, outer remnant of the endless capillary for creating the desired length 12 of the capillary 9;

Cutting off a second inner remnant of the capillary 9.

Cutting off the first outer remnant should take place very carefully and specifically, because the final volume of the packing 10 is fixed by this. In contrast thereto, the cutting off of the second inner remnant of the capillary 9 can be performed by simple bending, because the solid seat of the capillary 9 in the receiving opening 21 of the body 3 defines an exact bending area.

Several capillaries 9 can be inserted parallel, or several endless capillaries can be used for equipping a microplate with capillaries.

Like elements in the drawing figures have been provided with the same reference numerals, in this case the appropriate designations apply, even if they are not expressly mentioned in each case. Any arbitrary combinations of the represented, or described characteristics are parts of the present invention.

What is claimed is:

1. A microplate for processing samples, comprising:
   (a) a plurality of wells that constitute collecting chambers;
   (b) separating chambers for the solid phase extraction and elution of organic, or inorganic particles separated from these samples, the separating chambers adjoining the collecting chambers; and
   (c) openings for releasing these particles;
   wherein to each well of the assembled microplates is mounted a capillary that is connected with the collecting chamber, the capillary with a desired length and a defined diameter having been divided from a lengthy capillary with a capillary wall filled with a monolith packing of an organic or inorganic base material for solid phase extraction, which capillary comprises the release opening, and which capillary constitutes the separating chamber.

2. The microplate in accordance with claim 1, wherein each well is connected with a pump for aspirating and/or dispensing fluids, acting on this collecting chambers.

3. The microplate in accordance with claim 1, wherein the packing of each capillary directly adjoins the well.

4. The microplate in accordance with claim 1, wherein the packing completely fills each capillary.

5. The microplate in accordance with claim 1, wherein the packing in the capillaries is matched to the chemical-physical nature of the organic, or inorganic particles to be extracted.

6. The microplate in accordance with claim 1, wherein at least one ring-shaped area of each capillary and/or an area of the interior surface of each well directly adjoining this capillary, are made hydrophobic.

7. The microplate in accordance with claim 1, wherein each well has a V-shape, which adjoins the capillary in the area of its narrowest point.

8. The microplate in accordance with claim 1, wherein at least a portion of the interior surface of each well comprises a relief structure which extends essentially coaxially in respect to the longitudinal axis of the well.

9. The microplate in accordance with claim 1, wherein the microplate additionally has a support element with at least one depression, into which the microplate can be sealingly placed without a capillary being touched.

10. The microplate in accordance with claim 9, wherein the support element is embodied as a support plate, which has respectively one depression per well of the microplate.

11. The microplate in accordance with claim 10, wherein the support plate is made of polypropylene, or polypropylene foam, or similar solid, or elastic plastic materials.

12. A method of using the microplate according to claim 1, the method comprising solid phase extracting and eluting of particles separated from samples.

13. The method of claim 12, wherein the samples are subjected to an incubation step.

14. The method of claim 12, wherein each well of the microplate is connected to a pump for aspirating and/or dispensing fluids, acting on this collecting chambers.

15. A method for producing a microplate for processing samples, the microplate comprising:
   a plurality of wells that constitute collecting chambers;
   separating chambers for the solid phase extraction and elution of organic, or inorganic particles separated from these samples, the separating chambers adjoining the collecting chambers; and
   openings for releasing these particles;
   wherein to each well of the assembled microplates is mounted a capillary that is connected with the collecting chamber, which capillary comprises the release opening, and which capillary constitutes the separating chamber, whereby said packing is a monolith packing of an organic or inorganic base material for solid phase extraction and fills the whole cross-section of said capillary, the method being characterized by the following process steps:
   (a) dividing a lengthy capillary of a defined diameter and filled with a packing into capillaries of a desired length;
   (b) injection-molding a microplate with a plurality of wells, each one of which having a receiving opening for a partial capillary element;
   (c) inserting the capillaries through the wells.

16. The method in accordance with claim 15, wherein each well is connected to a pump for aspirating and/or dispensing fluids, acting on this collecting chambers.

17. A method for producing a microplate for processing samples, the microplate comprising:
   a plurality of wells that constitute collecting chambers;
   separating chambers for the solid phase extraction and elution of organic, or inorganic particles separated from these samples, the separating chambers adjoining the collecting chambers ; and
   openings for releasing these particles;
   wherein to each well of the assembled microplates is mounted a capillary that is connected with the collecting chamber, which capillary comprises the release opening, and which capillary constitutes the separating chamber, whereby said packing is a monolith of an organic or inorganic base material for solid phase extraction and fills the whole cross-section of said capillary, the method being characterized by the following process steps:
   (a) securing a plurality of lengthy capillaries of a defined diameter and filled with a packing in an injection mold cavity;
   (b) injection-molding a well of a microplate around each one of the secured lengthy capillaries,
   (c) cutting off a first, outer remnant of the lengthy capillaries for creating the desired length of the capillaries,
   (d) cutting off a second inner remnant of the capillaries.

18. The method in accordance with claim 17, wherein each well is connected to a pump for aspirating and/or dispensing fluids, acting on this collecting chambers.

* * * * *